United States Patent [19]

Clément et al.

[11] 4,346,115

[45] Aug. 24, 1982

[54] FERMENTATION OF ACID-CONTAINING DOUGHS

[75] Inventors: Philippe Clément, Roubaix; Jean-Paul Rossi, Marcq En Baroeul, both of France

[73] Assignee: Lesaffre et Cie, Paris, France

[21] Appl. No.: 863,950

[22] Filed: Dec. 23, 1977

[30] Foreign Application Priority Data

Dec. 24, 1976 [GB] United Kingdom ............... 54174/76

[51] Int. Cl.$^3$ .......................... A21D 2/14; C12C 11/16; C12N 1/18
[52] U.S. Cl. .......................................... 426/25; 426/19; 426/62; 435/245; 435/256
[58] Field of Search ........................ 426/60, 62, 20, 25, 426/18, 19; 435/256, 245

[56] References Cited

U.S. PATENT DOCUMENTS

| | | | |
|---|---|---|---|
| 1,727,847 | 2/1929 | White ................................... | 435/245 |
| 3,120,473 | 2/1964 | DeLoffre ............................. | 435/256 |
| 3,394,008 | 7/1968 | Lodder et al. ....................... | 426/19 |
| 3,617,306 | 11/1971 | Pomper et al. ....................... | 426/256 |
| 3,830,938 | 8/1974 | Morikawa et al. ................... | 426/18 |
| 3,922,350 | 11/1975 | Dockendirt et al. ................. | 426/25 |
| 3,993,783 | 11/1976 | Langejan et al. ..................... | 426/18 |

FOREIGN PATENT DOCUMENTS

1262648 2/1972 United Kingdom .

OTHER PUBLICATIONS

Reed, et al., Yeast Technology, The Avi Publ. Co. Inc., Westport, Conn., 1973, (pp. 21, 85, 96, 150).

*Primary Examiner*—David M. Naff

[57] ABSTRACT

Fermentation of acid-containing dough in bread-making is carried out with a baker's yeast in the form of compressed fresh yeast or dried yeast that has reduced inhibition to acid in the dough. The yeast is preferably prepared by selecting a strain of quick yeast, adapted to maltose and stable on conversation and drying, and cultivating the yeast by a process wherein during a last discontinuous cycle of multiplication of the yeast, a discontinuous flow of molasses is carried out by brief interruptions of flow.

7 Claims, No Drawings

FERMENTATION OF ACID-CONTAINING DOUGHS

BACKGROUND OF THE INVENTION

1. Field of the Invention

The invention relates to improvements in or to baker's yeast, these improvements consisting both in novel yeasts and in novel applications of already described yeasts and improved methods of preparation, it being recalled that said baker's yeasts can be in the form of fresh yeast with about 28 to 35% of dry matter or in the form of active dry yeast with more than 92% of dry matter.

2. Description of the Prior Art

It is known that bread-making yeasts are strongly inhibited by acetic acid and mixtures of acetic acid and lactic acid which are added or developed naturally by lactic bacteria within the scheme of certain bread-making operations such as sour leavened breads and rye breads as well as acid breads generally. It is known on the other hand, that bread-making yeasts are inhibited by mold inhibitors which are added to the dough on kneading, to increase the preservation of the bread. These mold inhibitors are, besides the acetic acid already mentioned as well as its salts, propionic and sorbic acids as well as their sodium and calcium salts.

Inhibition of the bread-making yeast leads to alteration of its fermentative power, that is to say, a loss in fermenting power which can exceed 66% according to tests carried out with the zymotachygraph, this alteration having the result either of the necessity to increase to very considerable proportions the amounts of yeast necessary, or the obtaining of breads which are little developed.

The degree of inhibition of the yeast depends on the concentration of the inhibitor organic substances and on the pH which intervenes in the percentage of dissociation of these substances. In fact, it would seem that it is essentially the organic acid in its undissociated form which has the inhibitor action.

This problem of inhibition of bread-making fermentation by acetic acid and mold inhibitors present in the dough concerns a part of bread-making in numerous countries.

It is an object of the invention to overcome these drawbacks.

GENERAL DESCRIPTION OF THE INVENTION

According to the invention, in order to achieve this, recourse is had either to novel bread-making yeasts in fresh form (pressed yeast) and in dried form (dry yeast), hence preferably adapted to maltose, little penalized by the presence of acetic acid and also, preferably, by the presence of other inhibitor acids and of their salts, or to yeasts already described for other applications.

Consequently, given that the tests* utilized are the following:

*The tests utilized are tests A, using the BURROW and HARRISON fermentometer and tests B, using the CHOPIN zymotachygraph.

Test $A_1$ (fresh compressed yeasts)

To 20 g of flour incubated at 30° C., is added a weight of compressed yeast corresponding to 160 mg of dry matter, this yeast being diluted in 15 ml of water containing 27 g of NaCl per liter and 4 g of $(NH_4)_2 SO_4$ per liter; it is mixed by means of a spatula for 40 seconds, so as to obtain a dough which is placed on a water bath adjusted to 30° C. Thirteen minutes after the starting of mixing, the vessel containing the dough is hermetically sealed; the total amount of gas produced is measured after 60, then 120 minutes; this amount is expressed in ml at 30° C. and under 760 mm of Hg.

Test $A'_1$ (dry yeasts)

Identical with test $A_1$, but prior to mixing, the dry yeast is rehydrated in distilled water at 38° C. For this purpose 40% of the hydration water applied is used; the complement of water, supplemented with 405 mg of NaCl, is added at the end of 15 minutes of rehydration.

Tests $A_5$ and $A'_5$

Tests identical respectively with tests $A_1$ and $A'_1$, with the difference that there is added to the yeast suspension, just before the addition of the latter to the flour, an amount of 0.15 ml of a mixture constituted by 15 g of acetic acid and 80 g of lactic acid, these 0.15 ml being substituted for 0.15 ml of the water of dilution.

Test $B_1$ (fresh compressed yeasts and instant dry yeasts not needing prior rehydration)

To 250 g of flour, is added a weight of compressed yeast or of instant dry yeast corresponding to 1.6 g of dry yeast material, and 150 ml of salt water (50 g of salt/1.5 l of water); it is kneaded for six minutes; the temperature of the dough must be 27° C. at the end of kneading. The dough is placed in the apparatus and six minutes, measured exactly, after the end of kneading, the vessel thermostated to 27° C. is placed under pressure. The total release recorded on a graph is measured, in ml, after 1 hour and 3 hours.

Test $B'_1$ (dry yeasts having to be rehydrated)

Test identical to test $B_1$, but prior to kneading, the dry yeast is rehydrated in distilled water at 38° C. (50 ml) for 15 minutes. The complement of water and of salt is added at the end of the 15 minutes of rehydration.

Test $B'_3$

Test identical with test $B'_1$, with the difference that added to the yeast suspension obtained after dilution of the fresh yeast or after rehydration of dry yeast, just before kneading, an amount of 2 ml of a mixture constituted by 15 g of acetic acid and 80 g of lactic acid, these 2 ml being substituted for 2 ml of diluting water. The invention comprises by way of novel industrial products the fresh yeasts giving more than 32 ml of $CO_2$ in test $A_5$ and, preferably, more than 35 ml of $CO_2$ in test $A_5$ and, even more preferably, more than 40 ml of $CO_2$ in test $A_5$ and more than 600 ml in test $B'_3$ and, preferably, more than 750 ml in test $B'_3$ and, even more preferably, more than 900 ml in test $B'_3$.

It relates also, by way of novel industrial products, to dry yeasts giving more than 28 ml in test $A'_5$ and, preferably, more than 32 ml in test $A'_5$ and, even more preferably, more than 35 ml in this test $A'_5$, and more than 500 ml in test $B'_3$ and, preferably, more than 625 ml in test $B'_3$ and, even more preferably, more than 750 ml in this test.

These results show that on doughs containing a proportion of organic acids inhibiting fermentation (that is to say release of $CO_2$) results superior to all known yeasts, the results of the preferred yeasts being even superior by more than 50% in the test $B'_3$ with the CHOPIN zymotachygraph to those obtained with known yeasts.

The invention relates also to the application to the fermentation of acid doughs, and/or containing mold inhibitors, of compressed fresh bread-making yeasts having the properties of those which are obtained by proceeding successively with:

the selection of a strain of quick yeast, adapted to maltose, stable on drying and stable on preservation, preparation of a compressed fresh yeast from the abovementioned strain by the application of the culture method comprising, on the last discontinuous multiplication cycle of the yeast, a discontinuous flow of molasses constituted preferably by brief interruptions of this flow.

In a preferred embodiment of said process, the discontinuous flow is constituted by flows of molasses of 5 to 10 minutes, followed by interruptions of 5 to 10 minutes, the total flow in one hour remaining always identical with that observed in the normal scheme with continuous flow of molasses.

The invention relates also to the application to the fermentation of acid and sour doughs and/or containing mold inhibitors of compressed fresh bread-making yeasts having the properties of those obtained from one of the strains of the group of strains deposited at the National Collection of Yeast Cultures and comprising:
the strain N.C.Y.C. 848
the strain N.C.Y.C. 847
as well as that deposited under number N.C.Y.C. R 30 and which, preferably, is previously adapted to maltose.

The invention relates also to the application to the fermentation of acid doughs and/or containing mold inhibitors, of compressed fresh bread-making yeasts having the properties of those which are obtained of any one of the strains N.C.Y.C. 848, N.C.Y.C. 847, and N.C.Y.C. R 30, preferably, previously adapted to maltose, the culture process used comprising, in the last discontinuous multiplication cycle of the yeast, a discontinuous flow of molasses constituted preferably by brief interruptions of this flow.

The invention relates lastly to the application to the fermentation of acid doughs and/or containing mold inhibitors of dry bread-making yeasts containing more than 92% of dry matter and having the properties of those which are obtained by the application of a convenient drying process, preferably a short process where the temperature of the yeast does not exceed 35° C., the drying technique being selected within the group comprising pneumatic drying and fluidized bed drying, said drying process being applied to one of the fresh yeasts whose application to the fermentation of acid doughs and/or containing mold inhibitors has just been indicated as an object of the invention.

This being so, it is indicated that slow strains, even very slow strains not adapted to maltose and having good resistance to inhibitor organic acids of which the strain N.C.Y.C. R 30, can be adapted to maltose by the addition of maltose in the 2 or 3 last hours of the multiplication cycle, so that the maltose constitutes a significant percent of the glucids assimilated by the yeast by multiplication during these last hours, applicant having found that this adaptation to maltose was obtained with all strains of which it was desired to improve this character and was partially conserved in the presence of inhibitor organic acids.

Firstly, a yeast strain is selected which is stable on conservation and stable on drying, having in the absence of inhibitor organic acids maximal properties for the application desired, then from this strain the compressed fresh yeast is prepared which will if necessary be dried subsequently, the method of propagation being such that it confers on said fresh yeast a very good resistance to inhibitors which is manifested generally by a fermentative activity very much higher than untreated controls, in the presence of organic acids at an inhibiting concentration.

As indicated above, said method of propagation comprises, on the last cycle of multiplication of yeast, a discontinuous flow of molasses constituted preferably by brief interruptions of this flow.

Lastly, by means of this method, it is easy to obtain yeasts rich in trehalose and with a very low proportion of buds. The results that are obtainable by means are perfectly reproducible.

When it is the fresh or dried yeasts obtained from strains N.C.Y.C. 848, N.C.Y.C. 847 and N.C.Y.C. R 30 which are applied to the fermentation of acid doughs and/or containing mold inhibitors, the propagation method used may be a conventional method with a continuous flow of molasses.

This being the case, even better results are obtained by applying to the fermentation of acid doughs and/or containing mold inhibitors, fresh or dried yeasts obtained from the abovesaid strains by applying the preferred propagation process comprising the above-described improvement.

In fact, the results have been improved by the order of 20%.

In any case, whether the propagation process used comprises or not the abovementioned improvements, it is conducted so that the fresh yeast harvested has a minimum budding ratio and an optimum composition, that is to say:

$$\frac{\text{trehalose}}{\text{dry matter}} \geq 12\%$$

composition of nitrogen and of $P_2O_5$ optimum for the strain and desired application (this composition only being determinable by successive experiments).

The yeasts are then harvested and put into the form of compressed bread yeast in known manner, when sale is done in the form of fresh yeast.

When the yeasts are intended to be dried this must be done by means of a particularly gentle method, the drying be done in the presence of emulsifying and stabilizing agents with suitable emulsifying and film-forming properties.

The drying process may be selected from the group comprising pneumatic drying and drying in a fluidized bed.

Although the multiplication of the hybrids of quick yeast, adapted to maltose by means of the propagation process described (discontinuous flow of molasses) does not permit the production of fresh yeasts having a release equal to or greater than 45 ml in the test $A_5$ and 1000 ml in the test $B'_3$ and dry yeasts having a gas release equal to or greater than 38 ml in the test $A'_5$ and 820 ml in the test $B'_3$, the new hybrids N.C.Y.C. 847 and N.C.Y.C. 848 enable these values to be exceeded without any special treatment, and to be very distinctly exceeded within the scope of the process indicated.

DESCRIPTION OF PREFERRED EMBODIMENTS

In order that the invention may be more clearly understood, the following examples are given purely by way of non-limiting illustration.

EXAMPLE 1

In the factory according to customary practices cultivation is carried out on a quick yeast hybrid adapted to maltose and the 3 strains NCYC R 30, NCYC 848 and NCYC 847.

The fresh yeast is produced in tanks of 200 m$^3$ containing before harvesting 100 m$^3$ of yeast-culture nutrient. The additions of molasses, sal ammoniac or ammonia, and biammonium phosphate are carried out continuously so as to obtain:

a nitrogen content to dry matter of about 8%,
a P$_2$O$_5$ content to dry matter of about 2.3%,
a trehalose content to dry matter of about 13%,
a bud ratio on the order of 1%.

At the beginning of fermentation, there were added the growth factors and vitamins necessary for each strain (biotin, group B vitamins, etc.).

At the end of production and before harvesting, the pH was greater than 6, and the alcohol in the tank was 0° Gay Lussac.

The yeast was separated on a separator, washed, dehydrated on a rotary filter under vacuum and made into loaves with about 32% of dry matter. Cryoscopic lowering of the external water of the pressed yeast obtained, measured by the method described in French patent 75 20943 is 0.3° C.

A part of the yeast was sampled at the exit from the rotary filter under vacuum and dried in the Laboratory after addition of an emulsion constituted by sorbitol ester and gum arabic under the same conditions as those described in Example 2 of French Pat. No. 75 20 943.

The results obtained for fresh yeast and those obtained for dried yeast are reported respectively in Tables I and II.

TABLE 1
FRESH YEASTS

| Strains | A$_1$ | A$_5$ | B$_1$ 1 h | B$_1$ 3 h | B'$_3$ 1 h | B'$_3$ 3 h |
|---|---|---|---|---|---|---|
| Hybrid of quick yeast adapted to maltose | 55 + 80 = 135 | 28 | 350 | 1700 | 60 | 400 |
| NCYC R 30 | 37 + 48 = 85 | 33 | 260 | 1200 | 120 | 650 |
| NCYC 848 | 60 + 80 = 140 | 53 | 420 | 1780 | 200 | 1160 |
| NCYC 847 | 55 + 75 = 130 | 50 | 400 | 1700 | 250 | 1200 |

TABLE II
DRIED YEASTS

| Strains | A'$_1$ | A'$_5$ | B$_1$ 1 h | B$_1$ 3 h | B'$_3$ 1 h | B'$_3$ 3 h |
|---|---|---|---|---|---|---|
| Hybrid of quick yeast adapted to maltose | 48 + 70 = 118 | 24 | 300 | 1500 | 45 | 300 |
| NCYC R 30 | 32 + 43 = 75 | 29.5 | 230 | 1050 | 90 | 500 |
| NCYC 848 | 51 + 68 = 119 | 43 | 350 | 1550 | 120 | 830 |
| NCYC 847 | 46 + 61 = 107 | 38 | 300 | 1470 | 110 | 830 |

EXAMPLE III

The two dry yeasts obtained with the hybrid of quick yeast adapted to maltose and with the strain NCYC R 30, were taken and they were tested comparatively in tests A'$_1$ and A'$_5$ adding 2 g then 4 g of Saccharose to the flour.

| | Quick Hybrid Dry Yeast Control | Dry Yeast NCYC R 30 |
|---|---|---|
| Test A'$_1$ | 48 | 32 |
| Test A'$_5$ | 24 | 29.5 |
| Test A'$_1$ + 2 g of saccharose | 41 | 47 |
| Test A'$_5$ + 2 g of saccharose | 15 | 45 |
| Test A'$_1$ + 4 g of saccharose | 28 | 36 |
| Test A'$_5$ + 4 g of saccharose | <10 | 34.5 |

EXAMPLE II

Under the same conditions as Example 1, the quick yeast hybrid adapted to maltose control was propagated with a discontinuous flow of molasses consisting of running for 10 minutes the flow which has to be done in 20 minutes and then interrupting for the 10 following minutes the flow of molasses.

A pressed yeast is obtained which is tested by tests B$_1$ and B'$_3$ which reproduce the fermentation conditions of breadmaking.

One obtains:

| Test B$_1$ | | Test B'$_3$ | |
|---|---|---|---|
| 1 h | 3 h | 1 h | 3 h |
| 390 | 1650 | 156 | 912 |

EXAMPLE IV

A direct breadmaking operation was carried out with a dough of the following composition (parts by weight):

| flour | 100 | sorbic acid | 0.08 |
|---|---|---|---|
| sugar | 2 | acetic acid acetate mixture | 0.33 |
| water | 60 | | |
| commercial pressed yeast | 2 | | |

The pH of the dough thus obtained was 5.3.

The tests carried out show that in this formula the commercial pressed yeast produced from a quick hybrid yeast can be replaced by dry yeast obtained in Example 1 from strain NCYC R 30 in the ratio 1/3.5.

The 2% of pressed yeast with respect to the flour can be replaced by 0.57% of dry yeast obtained with the strain NCYC R 30.

The current address for the National Collection of Yeast Cultures is: Agricultural Research Council's Food Institute, Colney Land, Norwich, Norfolk NR4 7UA, England.

I claim:

1. In the process of bread making wherein yeast is used to ferment sour doughs containing a source of at least one uncoated inhibitor acid of the class of acetic acid and sorbic acid, or to ferment doughs containing an acid mold inhibitor or salt thereof of the class of uncoated acetic acid, propionic acid, sorbic acid and their salts, the improvement comprising using as said yeast a fresh baker's yeast obtained by a fermentation process comprising the combination of
   (a) selecting a strain of quick yeast, adapted to maltose, stable on conservation and stable on drying, and (b) preparing a fresh compressed yeast from the aforesaid selected strain employing a multi-cycle multiplication process wherein a last discontinuous cycle for the multiplication of the yeast is carried out by a time-wise discontinuous flow of molasses comprising flows of molasses for 5 to 10 minutes, followed by interruptions for 5 to 10 minutes with the total molasses flow in one hour remaining always identical with that observed in a normal cultivation scheme with continuous flow of molasses, harvesting, separating, washing and filtering the thus-obtained yeast to obtain a compressed fresh baker's yeast, said baker's yeast having the properties of yielding (i) more than 40 ml of $CO_2$ in test $A_5$ in one hour, wherein in said test $A_5$, the said fresh baker's yeast in an amount corresponding to 160 mg of dry material, is diluted in the amount of water, as required to make up a total volume of 15 ml after the further addition, to said yeast suspension in water just before its mixing with flour, of 0.15 ml of a mixture of 15 g of acetic acid and 80 g of lactic acid in place of 0.15 ml of said dilution water, said water containing 27 g of NaCl and 4 g of $(NH_4)_2SO_4$ per liter, adding the resulting yeast/water/salt/acid mixture to 20 g of flour, incubated at 30° C., and then kneading the same for 40 seconds to obtain a dough, maintaining said dough at 30° C. in a vessel for 13 minutes after the beginning of said kneading, thereafter hermetically sealing said vessel and measuring the total amount of gas produced, in ml at 30° C. and 760 mm of Hg, after the expiration of 60 minutes; and (ii) more than 900 ml of $CO_2$ in test $B'_3$ in 3 hours, wherein, in said test $B'_3$ 1.6 g of yeast dry material is rehydrated at 38° C. with 50 ml of distilled water for 15 minutes, and at the end of said 15 minutes there is added thereto 2 ml of a mixture of 15 g of acetic acid and 80 g of lactic acid, with the remaining complement of water, i.e., 98 ml of water containing 5 g of salt, required to make up 150 ml total, the resulting yeast/water/salt/acid mixture being then added to 250 g of flour, and the resulting mixture is then kneaded for 6 minutes, so that the temperature of the resulting dough at the end of said kneading is 27° C., placing the dough in the chamber of a Chopin zymotachygraph, and exactly 6 minutes after said kneading, said chamber is placed under pressure and maintained at 27° C., and recording the total release of gas, in ml, on a graph after the expiration of 3 hours.

2. In the process of bread making wherein yeast is used to ferment sour doughs containing a source of at least one uncoated inhibitor acid of the class of acetic acid and sorbic acid, or to ferment doughs containing an acid mold inhibitor or salt thereof of the class of uncoated acetic acid, propionic acid, sorbic acid and their salts, the improvement comprising using as said yeast a fresh baker's yeast obtained by a multi-cycle fermentation process comprising the multiplication, harvesting, separating, washing and filtering to remove water, of one of the strains deposited at the National Collection of Yeast Cultures identified as strain number NCYC 848 or
strain number NCYC 847, said fresh baker's yeast thus obtained having the properties of yielding (i) more than 40 ml of $CO_2$ in test $A_5$ in 1 hour; wherein in said test $A_5$, the said fresh baker's yeast in an amount corresponding to 160 mg of dry material, is diluted in the amount of water, as required to make up a total volume of 15 ml after the further addition, to said yeast suspension in water just before its mixing with flour, of 0.15 ml of a mixture of 15 g of acetic acid and 80 g of lactic acid in place of 0.15 ml of said dilution water, said water containing 27 g of NaCl and 4 g of $(NH_4)_2SO_4$ per liter, adding the resulting yeast/water/salt/acid mixture to 20 g of flour, incubated at 30° C., and then kneading the same for 40 seconds to obtain a dough, maintaining said dough at 30° C. in a vessel for 13 minutes after the beginning of said kneading, thereafter hermetically sealing said vessel and measuring the total amount of gas produced, in ml at 30° C. and 760 mm of Hg, after the expiration of 60 minutes; and (ii) more than 900 ml of $CO_2$ in test $B'_3$ in 3 hours, wherein, in said test $B'_3$ 1.6 g of yeast dry material is rehydrated at 38° C. with 50 ml of distilled water for 15 minutes, and at the end of said 15 minutes there is added thereto 2 ml of a mixture of 15 g of acetic acid and 80 g of lactic acid, with the remaining complement of water, i.e., 98 ml of water containing 5 g of salt, required to make up 150 ml total, the resulting yeast/water/salt/acid mixture being then added to 250 g of flour, and the resulting mixture is then kneaded for 6 minutes, so that the temperature of the resulting dough at the end of said kneading is 27° C., placing the dough in the chamber of a Chopin zymotachygraph, and exactly 6 minutes after said kneading, said chamber is placed under pressure and maintained at 27° C., and recording the total release of gas, in ml, on a graph after the expiration of 3 hours.

3. The process according to claim 2, wherein said fresh baker's yeast has the properties of yielding more than 45 ml of $CO_2$, in said test $A_5$ in 1 hour, and more than 1000 ml of $CO_2$ in said test $B'_3$ in 3 hours.

4. The process according to claim 2 or 3, wherein the fresh baker's yeast is obtained by a multiplication process which uses in a last discontinuous cycle of multiplication of the yeast, a discontinuous flow of molasses comprising flows of molasses for 5 to 10 minutes, followed by interruptions for 5 to 10 minutes with the total molasses flow in one hour remaining always identical with that observed in a normal cultivation scheme with continuous flow of molasses.

5. In the process of bread making wherein yeast is used to ferment sour doughs containing a source of at least one uncoated inhibitor acid of the class of acetic acid, and sorbic acid, or to ferment a dough containing an acid mold inhibitor or salt thereof of the class of uncoated acetic acid, propionic acid, sorbic acid and their salts, the improvement comprising using as said yeast a dry baker's yeast which has been obtained by the combination of successive steps of:

(a) selecting a strain of quick yeast, adapted to maltose, stable on conservation and stable on drying, and (b) preparing a compressed fresh yeast from the aforesaid selected strain by employing a multi-cycle multiplication process wherein a last discontinuous cycle of the multiplication of the yeast is carried out by a time-wise discontinuous flow of molasses comprising flows of molasses for 5 to 10 minutes, followed by interruptions for 5 to 10 minutes with the total molasses flow in one hour remaining always identical with that observed in a normal cultivation scheme with continuous flow of molasses, harvesting, separating, washing and filtering the yeast obtained at the end of said last discontinuous cycle of multiplicaton, and (c) drying the said fresh yeast by employing a gentle drying process, by means of pneumatic drying of fluidized bed drying, said dry baker's yeast yielding (i) more than 35 ml in test $A'_5$ in 1 hour; wherein, in said test $A'_5$ 160 mg of dry matter of said dry yeast, which has been rehydrated in distilled water, at 38° C. with 40% of the volume of hydration used therefore, for 15 minutes, and thereafter adding thereto 0.15 ml of a mixture of 15 g of acetic acid and 80 g of lactic acid together with an amount of water containing 405 mg of NaCl, required to make up 15 ml, the yeast so rehydrated and mixed with said water additions is then added to 20 g of flour incubated at 30° C., kneading the resulting dough for 40 seconds to obtain dough, maintaining said dough at 30° C. in a vessel for 13 minutes after the beginning of said kneading, thereafter hermetically sealing said vessel and measuring the total amount of gas produced, in ml, at 30° C. and 760 mm of Hg, after the expiration of 60 minutes; and (ii) more than 750 ml of $CO_2$ in test $B'_3$ in 3 hours; wherein, in said test $B'_3$ 1.6 g of yeast dry material is rehydrated at 38° C. with 50 ml of distilled water for 15 minutes, and at the end of said 15 minutes there is added thereto 2 ml of a mixture of 15 g of acetic acid and 80 g of lactic acid, with the remaining complement of water, i.e., 98 ml of water containing 5 g of salt, required to make up 150 ml total, the resulting yeast/water/salt/acid mixture being then added to 250 g of flour, and the resulting mixture is then kneaded for 6 minutes, so that the temperature of the resulting dough at the end of said kneading is 27° C., placing the dough in the chamber of a Chopin zymotachygraph, and exactly 6 minutes after said kneading, said chamber is placed under pressure and maintained at 27° C., and recording the total release of gas, in ml, on a graph after the expiration of 3 hours.

6. In the process of bread making wherein yeast is used to ferment sour doughs containing a source of at least one uncoated inhibitor acid of the class of acetic acid, and sorbic acid, or to ferment a dough containing an acid mold inhibitor or salt thereof of the class of uncoated acetic acid, propionic acid, sorbic acid and their salts, the improvement comprising using a dry baker's yeast which has been obtained by the combination of successive steps of:

selecting one of the strains deposited at the National Collection of Yeast Cultures under the strain number NCYC 848 or NCYC 847, multiplying the said selected strain, harvesting, separating, washing, filtering the said yeast so as to obtain a fresh yeast adapted for drying;

and drying the said fresh yeast by employing a gentle drying process, by means of pneumatic drying or fluidized bed drying; the resulting dry baker's yeast yielding more than 38 ml in test $A'_5$ in one hour; wherein, in said test $A'_5$ 160 mg of dry matter of said dry yeast, which has been rehydrated in distilled water, at 38° C. with 40% of the volume of hydration used therefor, for 15 minutes, and thereafter adding thereto 0.15 ml of a mixture of 15 g of acetic acid and 80 g of lactic acid together with an amount of water containing 405 mg of NaCl, required to make up 15 ml, the yeast so rehydrated and mixed with said water additions is then added to 20 g of flour incubated at 30° C., kneading the resulting dough for 40 seconds to obtain dough, maintaining said dough at 30° C. in a vessel for 13 minutes after the beginning of said kneading, thereafter hermetically sealing said vessel and measuring the total amount of gas produced, in ml, at 30° C. and 760 mm of Hg, after the expiration of 60 minutes; and (ii) more than 820 ml of $CO_2$ in test $B'_3$ in 3 hours; wherein, in said test $B'_3$ 1.6 g of yeast dry material is rehydrated at 38° C. with 50 ml of distilled water for 15 minutes, and at the end of said 15 minutes there is added thereto 2 ml of a mixture of 15 g of acetic acid and 80 g of lactic acid, with the remaining complement of water, i.e., 98 ml of water containing 5 g of salt, required to make up 150 ml total, the resulting yeast/water/salt/acid mixture being then added to 250 g of flour, and the resulting mixture is then kneaded for 6 minutes, so that the temperature of the resulting dough at the end of said kneading is 27° C., placing the dough in the chamber of a Chopin zymotachygraph, and exactly 6 minutes after said kneading, said chamber is placed under pressure and maintained at 27° C., and recording the total release of gas, in ml, on a graph after the expiration of 3 hours.

7. An active dry baker's yeast composition containing an emulsifying agent and having more than 92% of dry matter for use in fermenting sour dough on dough containing an acid mold inhibitor or salt thereof, and wherein said dry yeast composition (a) yields more than 38 ml in test $A'_5$ in one hour, wherein, in said test $A'_5$ 160 mg of dry matter of said dry yeast, which has been rehydrated in distilled water, at 38° C. with 40% of the volume of hydration used therefor, for 15 minutes, and thereafter adding thereto 0.15 ml of a mixture of 15 g of acetic acid and 80 g of lactic acid together with an amount of water containing 405 mg of NaCl, required to make up 15 ml, the yeast so rehydrated and mixed with said water additions is then added to 20 g of flour incubated at 30° C., kneading the resulting dough for 40 seconds to obtain dough, maintaining said dough at 30° C. in a vessel for 13 minutes after the beginning of said kneading, thereafter hermetically sealing said vessel and measuring the total amount of gas produced, in ml, at 30° C. and 760 mm of Hg, after the expiration of 60 minutes; and (b) yields more than 820 ml in test $B'_3$ in 3 hours, wherein, in said test $B'_3$ 1.6 g of yeast dry material is rehydrated at 38° C. with 50 ml of distilled water for 15 minutes, and at the end of said 15 minutes there is added thereto 2 ml of a mixture of 15 g of acetic acid and 80 g of lactic acid, with the remaining complement of water, i.e., 98 ml of water containing 5 g of salt, required to make up 150 ml total, the resulting yeast/water/salt/acid mixture being then added to 250 g of flour, and the resulting mixture is then kneaded for 6 minutes, so that the temperature of the resulting dough at the end of said kneading is 27° C., placing the dough in the chamber of a Chopin zymotachygraph, and exactly 6 minutes after said kneading, said chamber is placed under pressure and maintained at 27° C., and recording the total release of gas, in ml, on a graph after the expiration of 3 hours.

* * * * *

UNITED STATES PATENT AND TRADEMARK OFFICE
CERTIFICATE OF CORRECTION

PATENT NO. : 4,346,115
DATED : August 24, 1982
INVENTOR(S) : Philippe Clement

It is certified that error appears in the above-identified patent and that said Letters Patent is hereby corrected as shown below:

On the title page, Item [75] should read:

-- [75] Inventor: Philippe Clement, Roubaix, France --.

Item [56] References Cited "Dockendirt" should read

-- Dockendorf --.

Column 9, line 12, "of" should read -- or --.
Column 10, line 33, "on" should read -- or --.

Signed and Sealed this

Thirty-first Day of May 1983

[SEAL]

Attest:

DONALD J. QUIGG

*Attesting Officer*     *Acting Commissioner of Patents and Trademarks*